US009585682B2

(12) United States Patent
Juanpera (10) Patent No.: US 9,585,682 B2
(45) Date of Patent: Mar. 7, 2017

(54) PORTABLE STAND-ALONE DEVICE, PARTICULARLY SUITABLE FOR USE IN SURGERY, MICRO-COMPONENT HANDLING AND THE LIKE (76) Inventor: Jesus Hernandez Juanpera, Barcelona (ES)

(*) Notice: Subject to any disclaimer, the term of this patent is extended or adjusted under 35 U.S.C. 154(b) by 790 days.

(21) Appl. No.: 13/994,195

(22) PCT Filed: Nov. 23, 2011

(86) PCT No.: PCT/ES2011/070810
§ 371 (c)(1),
(2), (4) Date: Sep. 9, 2013

(87) PCT Pub. No.: WO2012/080543
PCT Pub. Date: Jun. 21, 2012

(65) Prior Publication Data
US 2014/0371761 A1 Dec. 18, 2014

(30) Foreign Application Priority Data
Dec. 17, 2010 (ES) .................................. P201031876

(51) Int. Cl.
A61B 17/28 (2006.01)
A61B 34/00 (2016.01)
(Continued)

(52) U.S. Cl.
CPC .......... A61B 17/2804 (2013.01); A61B 17/29 (2013.01); A61B 34/70 (2016.02);
(Continued)

(58) Field of Classification Search
CPC .......... A61B 2017/00398; A61B 17/29; A61B 2017/2926; A61B 19/22
See application file for complete search history.

(56) References Cited

U.S. PATENT DOCUMENTS 5,538,305 A 7/1996 Conway
2004/0159169 A1 8/2004 Muramatsu
(Continued)

FOREIGN PATENT DOCUMENTS

EP 1627707 2/2006
JP 2002263109 9/2002

Primary Examiner — Katherine M Shi
Assistant Examiner — Michael Mendoza
(74) Attorney, Agent, or Firm — Sturm & Fix LLP (57) ABSTRACT The invention relates to a portable stand-alone device (1), particularly suitable for use in surgery, micro-component handling and the like. The invention comprises: a micro-tool that can be removably coupled to a main casing (3); and actuation means for handling the micro-tool (2), associated with servomotors. The aforementioned actuation means comprise: a first actuator associated with a first servomotor (4), providing the micro-tool (2) with a degree of rotational freedom; a second actuator associated with a second servomotor and connected to the first actuator in order to move the micro-tool forwards and backwards in translation; and a third actuator (6) associated with a third servomotor, which oscillates the micro-tool in relation to the longitudinal axis of the first and second actuators. The first, second and third actuators are associated with a control unit (7) for determining the position of the micro-tool in space.

20 Claims, 11 Drawing Sheets (51) Int. Cl.
*A61B 17/29* (2006.01)
*B25J 15/02* (2006.01)
*B25J 7/00* (2006.01)
*A61B 17/00* (2006.01)

(52) U.S. Cl.
CPC ............... *A61B 34/75* (2016.02); *B25J 7/00* (2013.01); *B25J 15/022* (2013.01); *A61B 34/30* (2016.02); *A61B 2017/00477* (2013.01); *A61B 2017/2927* (2013.01); *A61B 2017/2931* (2013.01); *A61B 2034/742* (2016.02)

(56) References Cited

U.S. PATENT DOCUMENTS

| | | | |
|---|---|---|---|
| 2006/0182606 A1 | 8/2006 | Mochizuki | |
| 2008/0283577 A1* | 11/2008 | Boyden | A61B 17/068 227/181.1 |
| 2009/0095790 A1* | 4/2009 | Whitman | A61B 17/07207 227/175.1 |
| 2010/0312103 A1* | 12/2010 | Gorek | A61B 6/12 600/425 |
| 2011/0130773 A1* | 6/2011 | Saliman | A61B 17/0469 606/145 |

\* cited by examiner

PORTABLE STAND-ALONE DEVICE, PARTICULARLY SUITABLE FOR USE IN SURGERY, MICRO-COMPONENT HANDLING AND THE LIKE

OBJECT OF THE INVENTION

The purpose of the invention patent application herein is to register a portable stand-alone device that incorporates significant innovations and advantages.

More specifically, the invention proposes the development of a portable stand-alone device, particularly suitable for use in surgery, micro-component handling and the like. The micro-tool can be removably coupled to a main casing and actuation means for handling the micro-tool associated with servomotors, making it easier to use and providing ample freedom of movement of the micro-tool during use. The fact that it can be removed facilitates cleaning and sterilisation.

BACKGROUND OF THE INVENTION

Robot arms having a tool coupled to their free end to make it possible to handle objects or parts of reduced dimensions in order to create assemblies or devices are well known in the state of the art; however, this type of robot has a reference point or fixed base, therefore limiting its use to the point where said robot arm is located.

Furthermore, the applicant is unaware of the existence of an invention that has all the characteristics which are described herein, which makes it possible to apply the working precision of a robotic arm to an instrument which is manually operable by a user.

DESCRIPTION OF THE INVENTION

The invention herein has been developed with the aim of providing a portable stand-alone device that resolves the aforementioned drawbacks, further providing other additional advantages that will be apparent from the description detailed hereinafter.

It is therefore an object of this invention to provide a portable stand-alone device, particularly suitable for use in surgery, of the type comprising a micro-tool that can be removably coupled to a main casing and actuation means for handling the micro-tool associated with servomotors, allowing the handler or user to work in a simple manner and completely autonomously, with high accuracy in respect of the spatial position of the electronic device of this invention during use. Handling this device is similar to holding a writing utensil.

This device may be particularly useful in microsurgery applications, micro-assembly, preparation of dental applications and micro-handling of biological structures.

It is therefore an object of this invention to provide a portable stand-alone device particularly suitable for use in surgery, comprising a micro-tool that can be removably coupled to a main casing and actuation means for handling the micro-tool associated with servomotors, allowing the handler or user work in a simple manner and with high accuracy in respect of the spatial position during use.

More particularly, the actuation means comprises a first actuator associated with a first servomotor providing the micro-tool with a degree of rotational freedom in respect of an axis that protrudes from the first servomotor; a second actuator associated with a second servomotor, connected to the first actuator in order to move the micro-tool forwards and backwards in translation, and a third actuator associated with a third servomotor for performing an oscillating movement of the micro-tool in relation to the longitudinal axis of the first and second actuators, with the first, second and third actuators associated with a control unit housed in the main casing for determining the position of the micro-tool in space; and wherein the actuation means are fed autonomously by at least one battery.

According to another aspect of the invention, the control unit may include a gyroscopic sensor associated with the microprocessor in order to stabilise the position of the micro-tool on the three coordinate axes, absorbing or eliminating any unwanted minimal hand movement or trembling of the user's hand when carrying out manual work with the device.

In a preferred embodiment, the control unit includes a motion detector associated with the microprocessor for detecting the position and acceleration on the three coordinate axes. By using this application, the user is expected to avoid having to stop holding the device to perform or order different actions. Thus, the device of the invention can be accurately positioned in a spatially defined position and this can be repeated indefinitely, allowing to program limit areas via the display or by acoustic or voice signals, whereby the user can place the micro-tool in a correct spatial position.

According to another characteristic, the control unit may include a voice recognition control or can even be controlled by wrist gestures to input orders into the microprocessor.

Advantageously, the microprocessor of the control unit can include an arithmetic logic unit which can determine, in real time, the corrective positioning values to be applied in respect of the spatial position of the micro-tool at a given time.

Other particular embodiments of the device of the invention are described in the dependent claims attached.

Other characteristics and advantages of the portable stand-alone device object of the invention herein will become apparent from the description of a preferred, although not exclusive embodiment, which is illustrated by way of non-limiting example in the drawings appended, in which:

DESCRIPTION OF A PREFERRED EMBODIMENT

As shown in the attached figures, a portable stand-alone device according to an embodiment of the invention, indicated generally by reference 1, is particularly useful in the field of surgery and for handling micro-components, essentially comprising a micro-tool that can be removably coupled to a main casing 3 formed by a substantially cylindrical and internally hollow hand-held body, and actuation means for handling the tool associated with a series of servomotors, which are described below.

Figure 1:
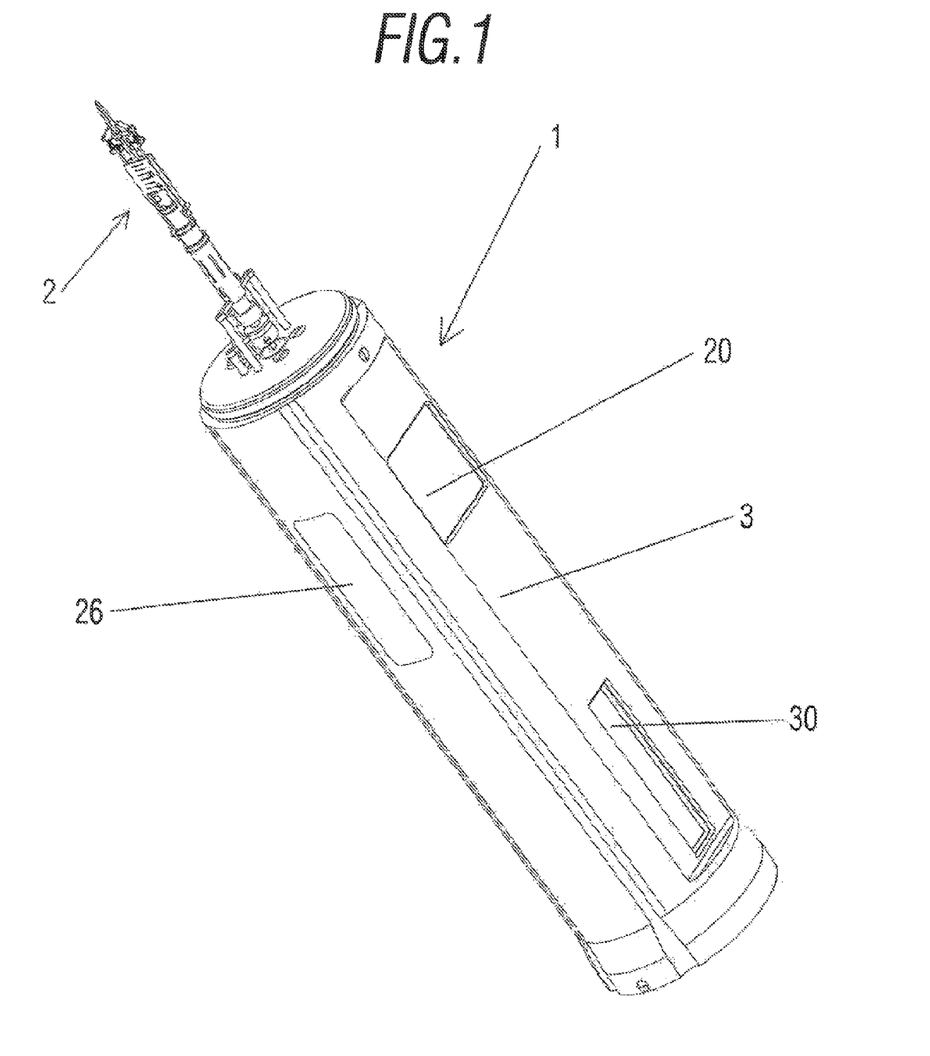
FIG. 1.—Perspective view of the portable stand-alone device according to the invention herein.
Figure 2:
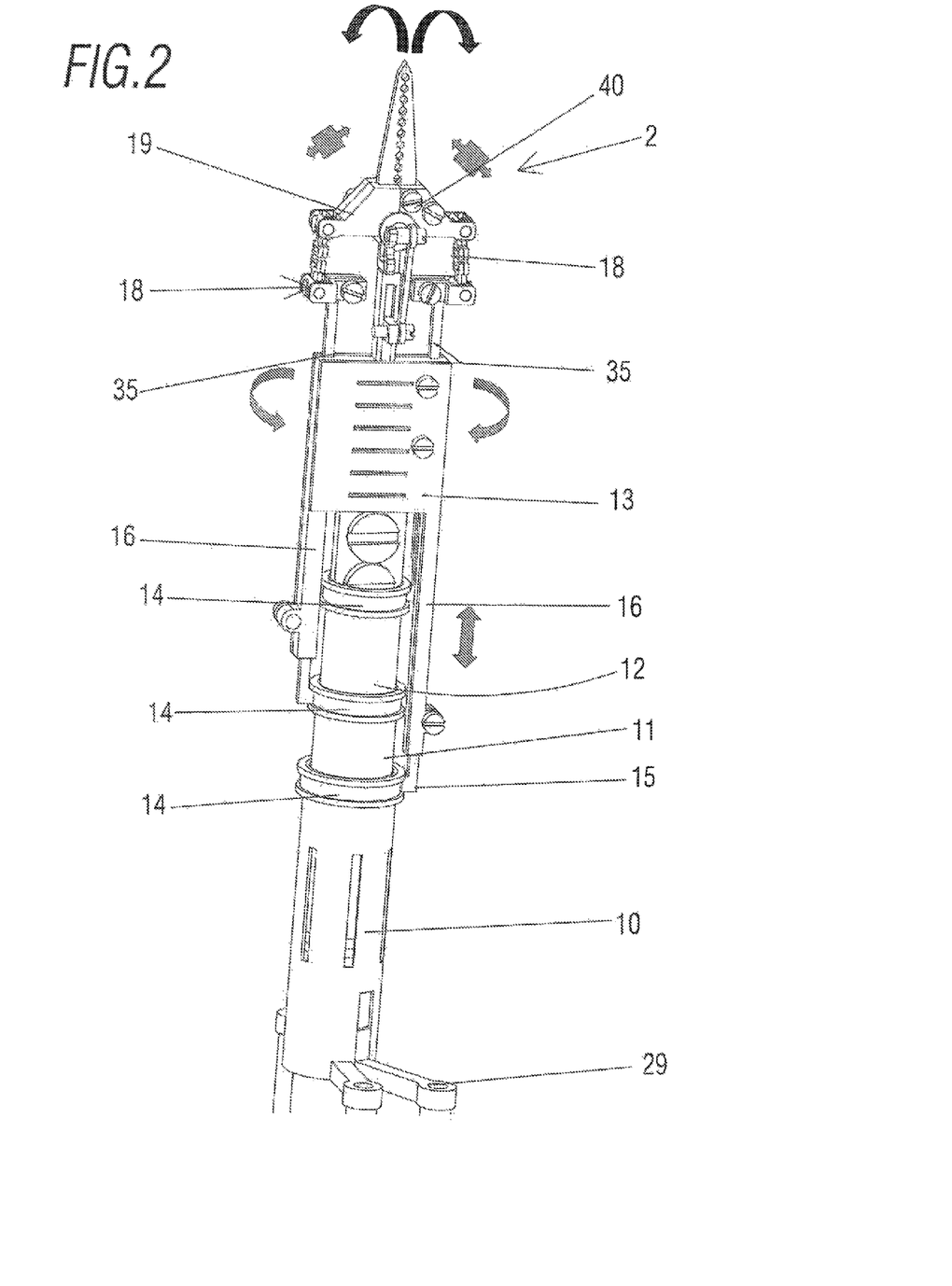
FIG. 2.—Detailed perspective view of the actuation means provided in the portable device of the invention.
Figure 3:
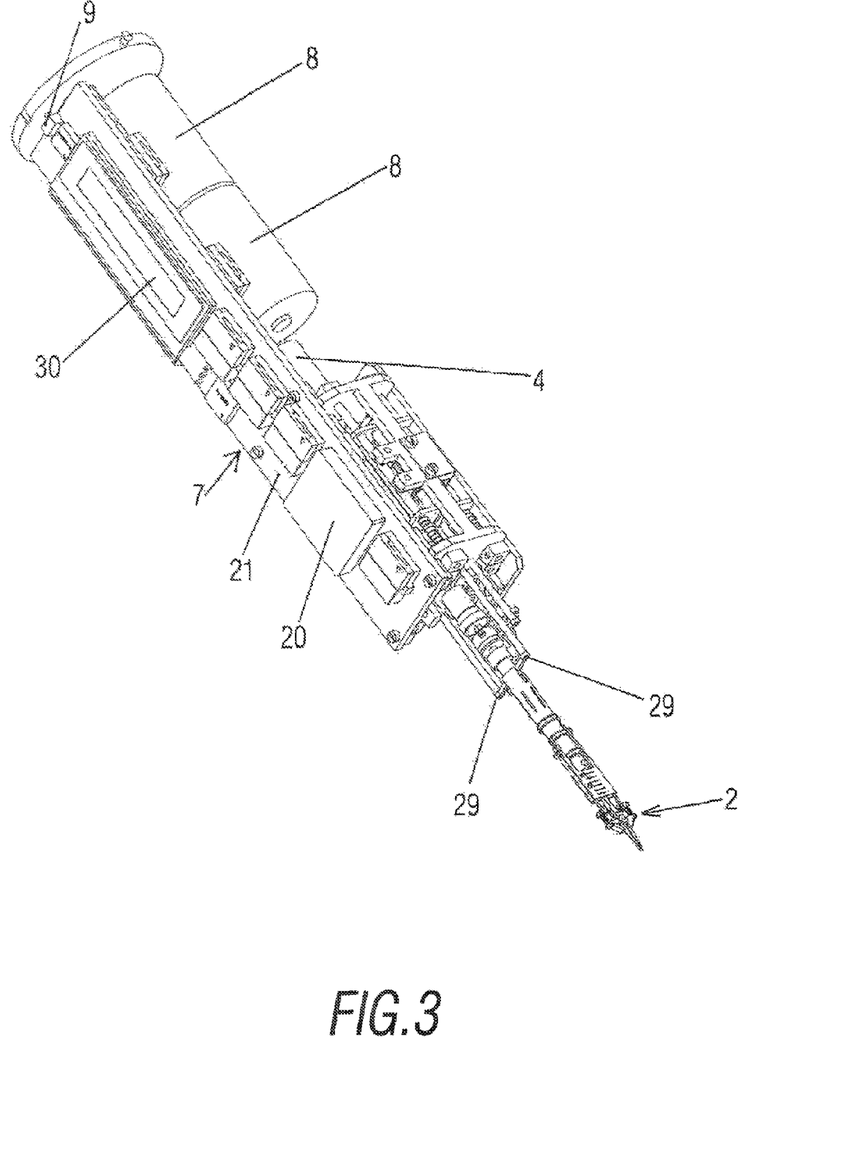
FIG. 3.—Perspective view of the portable device with the micro-tool in which the main casing has been removed.

The actuation means comprise a first actuator associated with a first servomotor 4, providing the micro-tool 2 with a degree of rotational freedom in relation to an elongated axis 5 and located centrally that protrudes from the first servomotor 4; a second actuator associated with at least a second servomotor 36, connected to the first actuator in order to move the micro-tool 2 forwards and backwards in translation; and a third actuator associated with a third servomotor 6, which allows the micro-tool 2 to oscillate in relation to the longitudinal axis 5 of the first and second actuators. In FIG. 2 the various movements which the moving parts in the actuation means and micro-tool perform are indicated by arrows.

The first, second and third actuators are associated with a control unit, generally indicated by reference 7, housed in the main casing 3 which can determine the position of the micro-tool in space.

The actuation means are powered independently by a pair of batteries 8 arranged in series located at the bottom end of the main housing 3. To determine if the device is on or off, a light-emitting diode 9 light source is provided that is also located close to the rear end of the main casing 3.

The abovementioned second actuator comprises three tubular bodies 10, 11 and 12 which can be extended telescopically with respect to each other, inside of which the aforementioned axis 5 of the first actuator runs along, wherein each tubular body is connected to a separate servomotor and in which guide means are provided to facilitate the rotational movement of the micro-tool 2.

The micro-tool 2 is joined to a connector element 13 having a substantially parallelepiped shape that is fixed to the axis 5 of the first actuator.

Making particular reference to the guide means: they consist of a number of grooves 14 provided with each of the respective tubular bodies 10, 11, 12 in an area close to the end edge, into which guide sections arranged on the connector element 13 are inserted, which can move along the entire diameter of the tubular bodies with an unlimited swivel angle since there are no wires or connectors present that limit the rotational capacity.

As seen more clearly in FIG. 2, the guide sections consist of L-shaped elements 15, the end of which fit in both grooves 14, which protrude and extend downwardly in relation to a number of hollow extensions 16 that are in the connector element 13.

Figure 4:
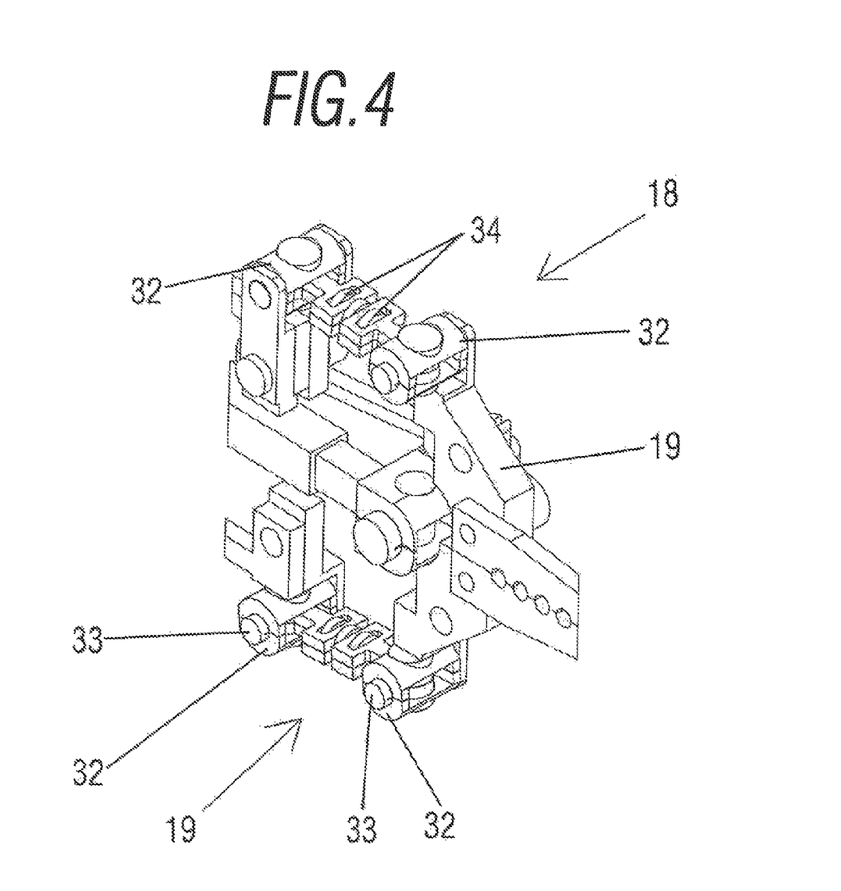
FIG. 4.—Detailed perspective view of one of the articulations associated with the tool holder and the connector element.

The third actuator comprises a pair of articulations 18 which are attached to the connector element 13 at one end and connected to the micro-tool 2 at the opposite end. These articulations 18 are seen in greater detail in FIG. 4 where the arrangement of two articulation end portions 32 secured by pins 33 is seen, between which a number of disks 34 are arranged. Furthermore, each of the articulations 18 can move longitudinally in relation to the axis of the device due to the presence of a number of extendable guides 35 which protrude from the connector element 13, those extendable guides 35 being an extension of the L-shaped elements 15.

The articulations 18 are manufactured by means of lithographic techniques due to their reduced size, where the various parts are obtained from multiple flat layers. In this manner, articulations with discontinuous jump or spherical or curved surfaces are avoided, to achieve a smooth, linear motion.

More specifically, the pair of articulations 18 is connected to a micro-tool 2 via a tool holder 19 that has fastening means for attaching the micro-tool, such fastening means being an aperture through which a screw passes 40, therefore exchanging the micro-tool is simple and fast.

Thanks to the constructive configuration, the components directly coupled to the micro-tool 2 by means of the connector element 13 (including its axis 5) can be removed together in relation to the rest of the device 1 quickly and easily, by means of screws 38 connected to the axis 5 and the connector element 13, such that the micro-tool 2 can be sterilised for surgical work or work requiring sterilisation.

Figure 7:
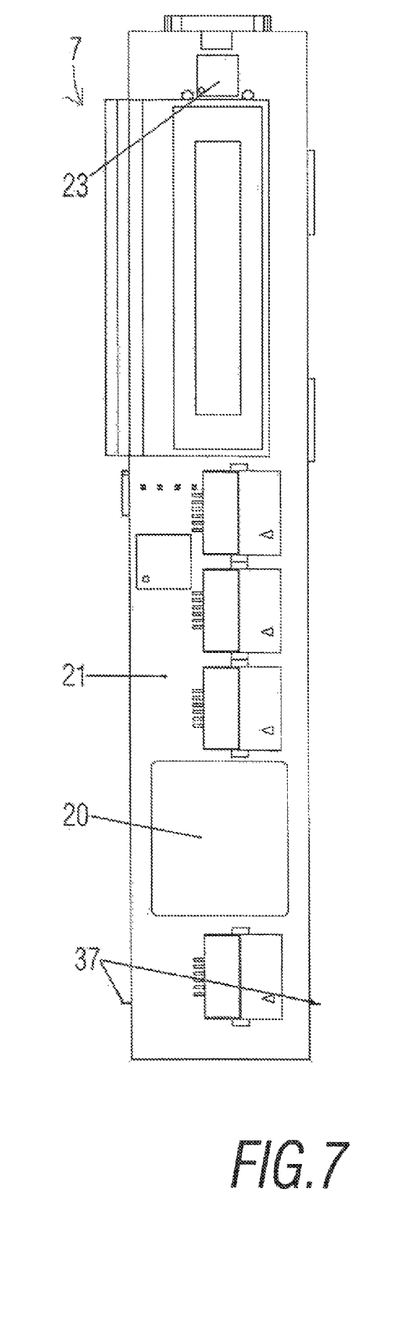
FIG. 7.—Schematic upper plan view of the control unit that operates the device of the invention.
Figure 8:
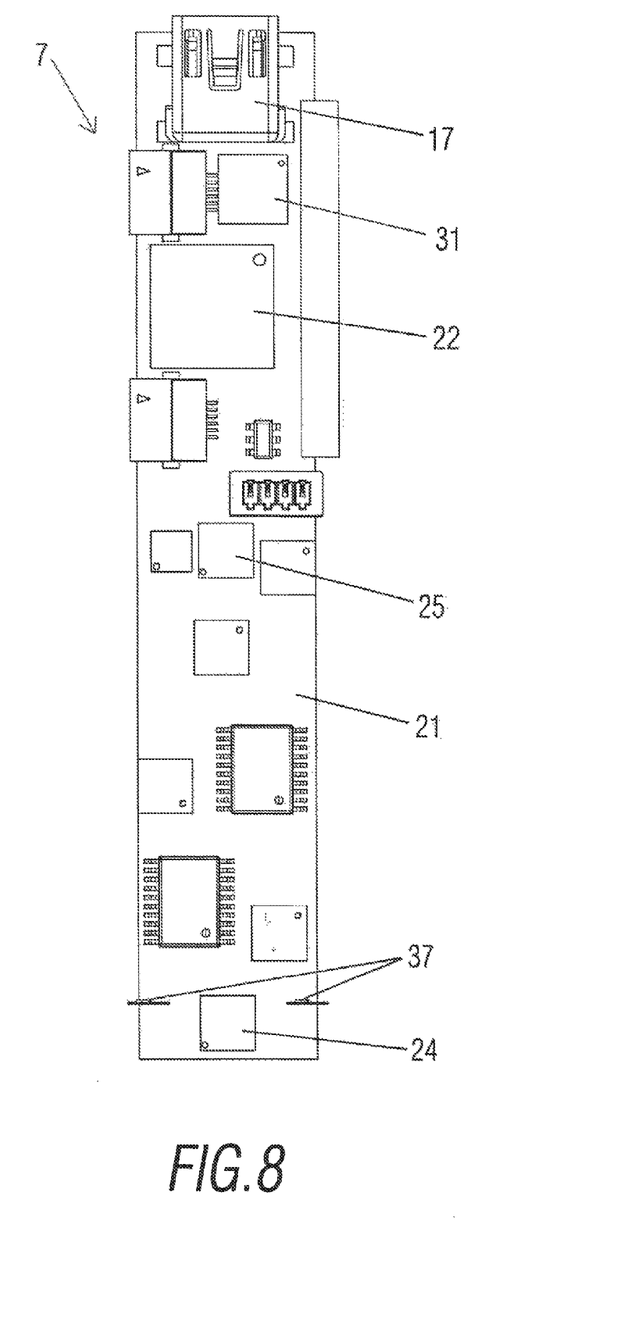
FIG. 8.—Schematic lower plan view of the control unit.

Referring now to FIGS. 7 and 8, the control unit 7 has a rectangular support plate 21 which is fixed inside the main casing 3.

The control unit 7 has a microprocessor 22 provided with a programmable memory associated with software that offers an extensive menu of variables that can be adapted according to requirements. The microprocessor 22 can be equipped with a voice recognition control and communications module 31 formed by a wireless communication system, such as for example Bluetooth or Wi-Fi, in order to communicate with other network devices. Other options include speech recognition commands.

The microprocessor 22 can recognise actions via wrist gestures, and actions controlled by the user can be programmed through combined actions of movement of the device itself.

The control unit 7 includes a motion detector 23 associated with the microprocessor 22 for detecting the position and acceleration on the three coordinate axes.

The control unit 7 includes a gyroscopic sensor 24 associated with the microprocessor 22 to stabilise the position of the micro-tool on the three coordinate axes X, Y and Z, such that trembling of the user's wrist can be corrected.

Additionally, the control unit 7 includes a geomagnetic sensor 25 associated with the microprocessor 22 such that the device can recognise with great accuracy which spatial position and orientation the portable device is in at all times in relation to the geomagnetic field and determine the optimum position for the micro-tool 2, as well as an external connection for coupling an external electronic device, such as a USB port 17.

The actuation means further comprise a pair of pushbuttons 26 located on two opposite ends of the outer face of the main casing 3; the aforementioned pushbuttons 26 being provided with a tactile pressure sensor that enables orders to be transmitted to the control unit 7.

Figure 5:
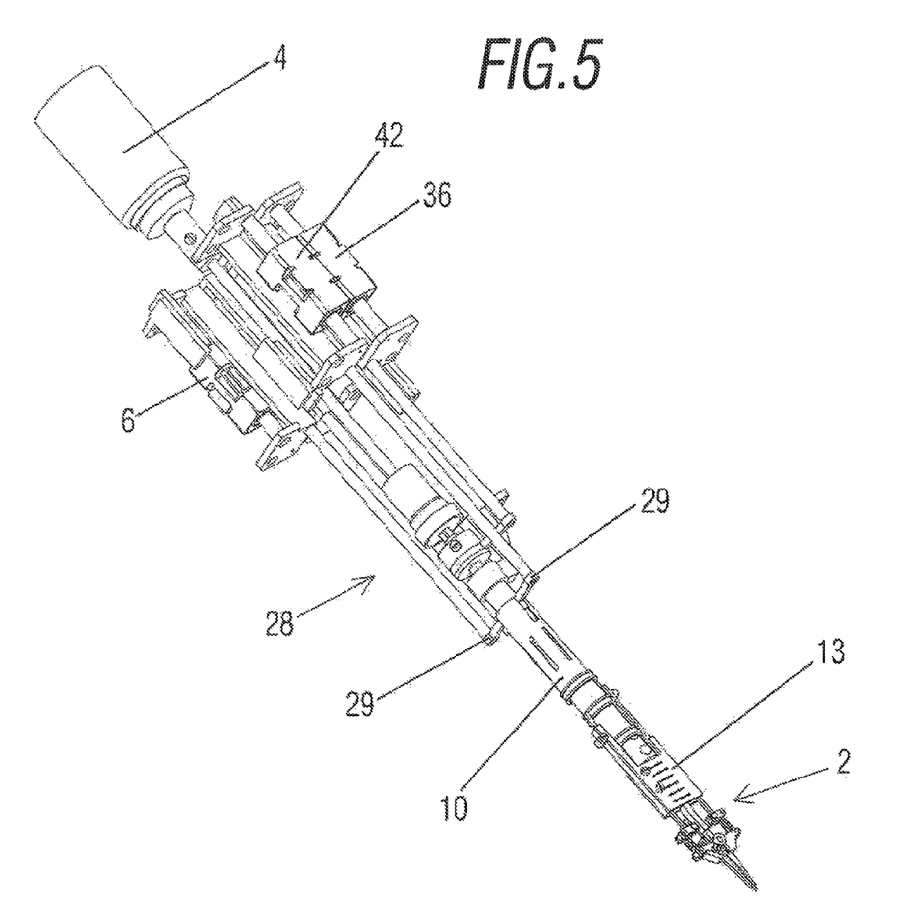
FIG. 5.—Perspective view of the portable device with the micro-tool in which the main casing and the control unit have been removed.
Figures 6A, 6D:
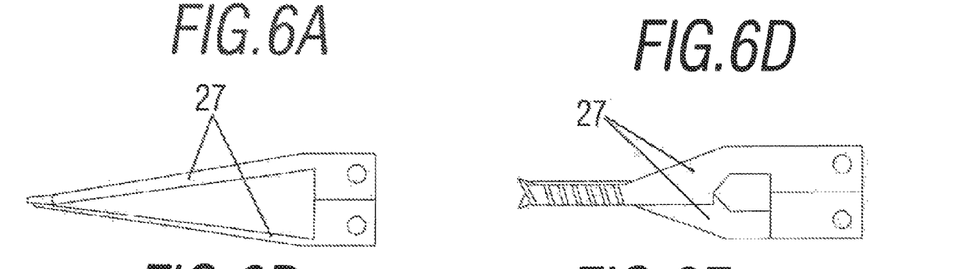
FIGS. 6A-6F.—Elevational views of different embodiments of the micro-tool.
Figure 6B:
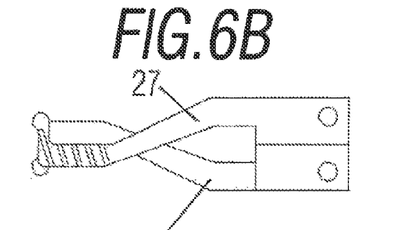
Figure 6C:
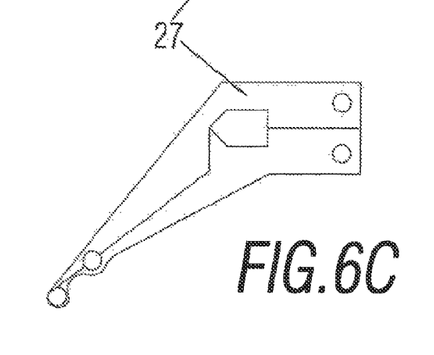
Figure 6E:
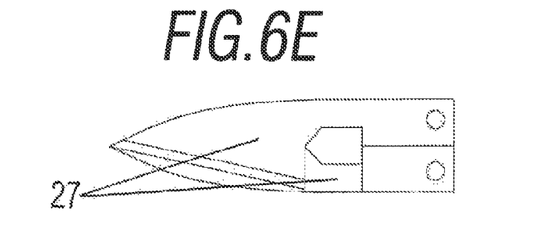
Figure 6F:
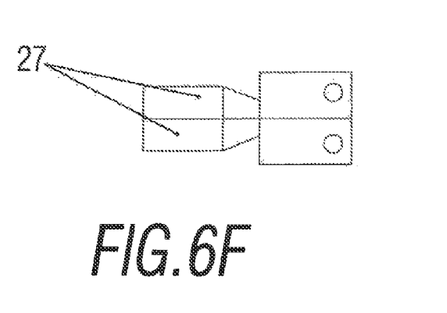
Figure 9A:
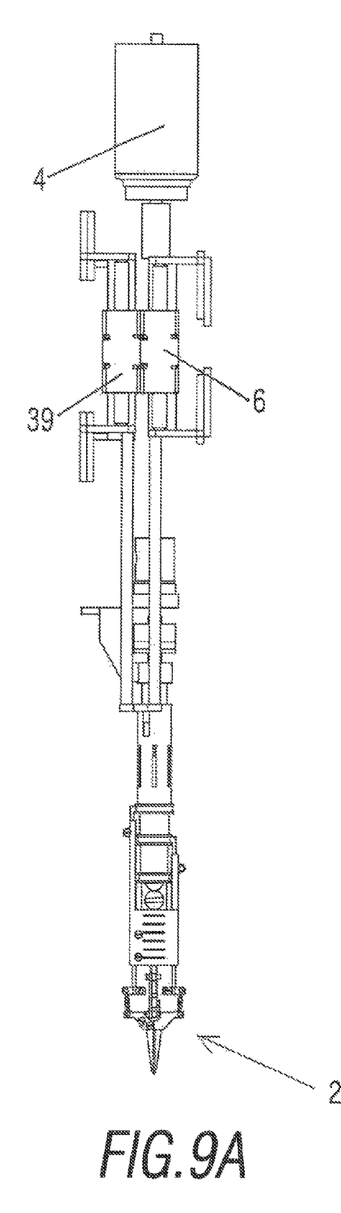
FIGS. 9A and 9B.—Elevation and plan view, respectively, of the inside of the device of the invention wherein some elements have been removed to facilitate comprehension.
Figure 9B:
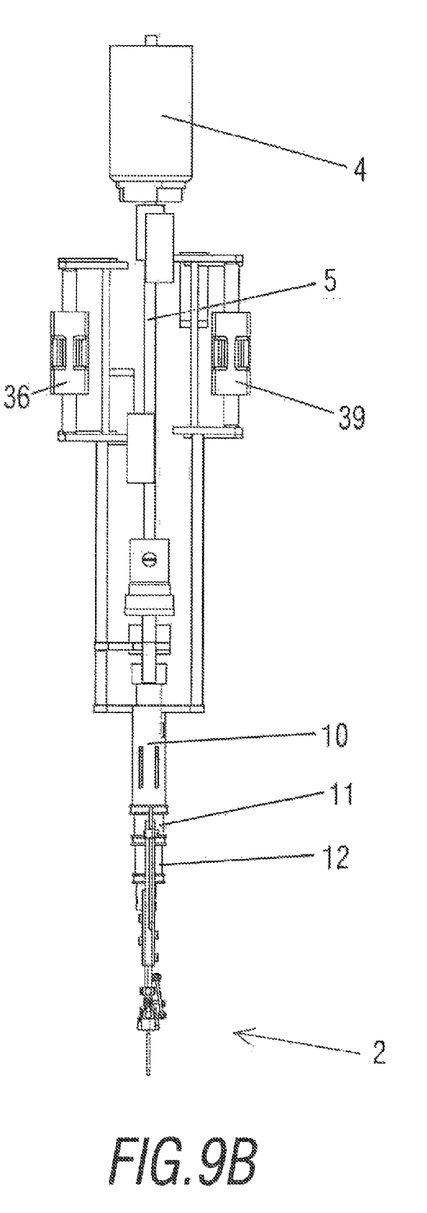
Figure 10:
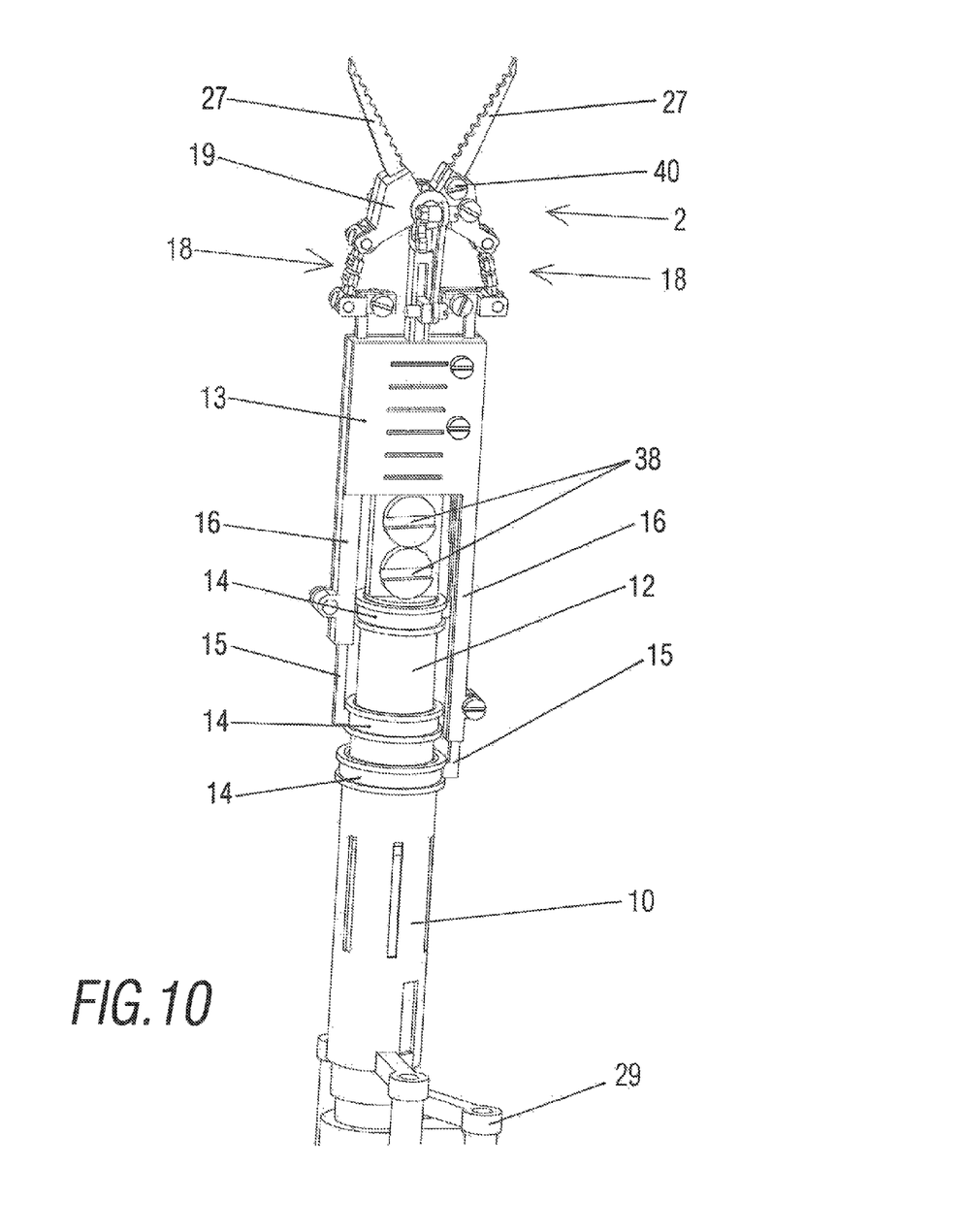
FIG. 10.—Perspective view of the section which houses the micro-tool in a position with the clamp open.
Figure 11:
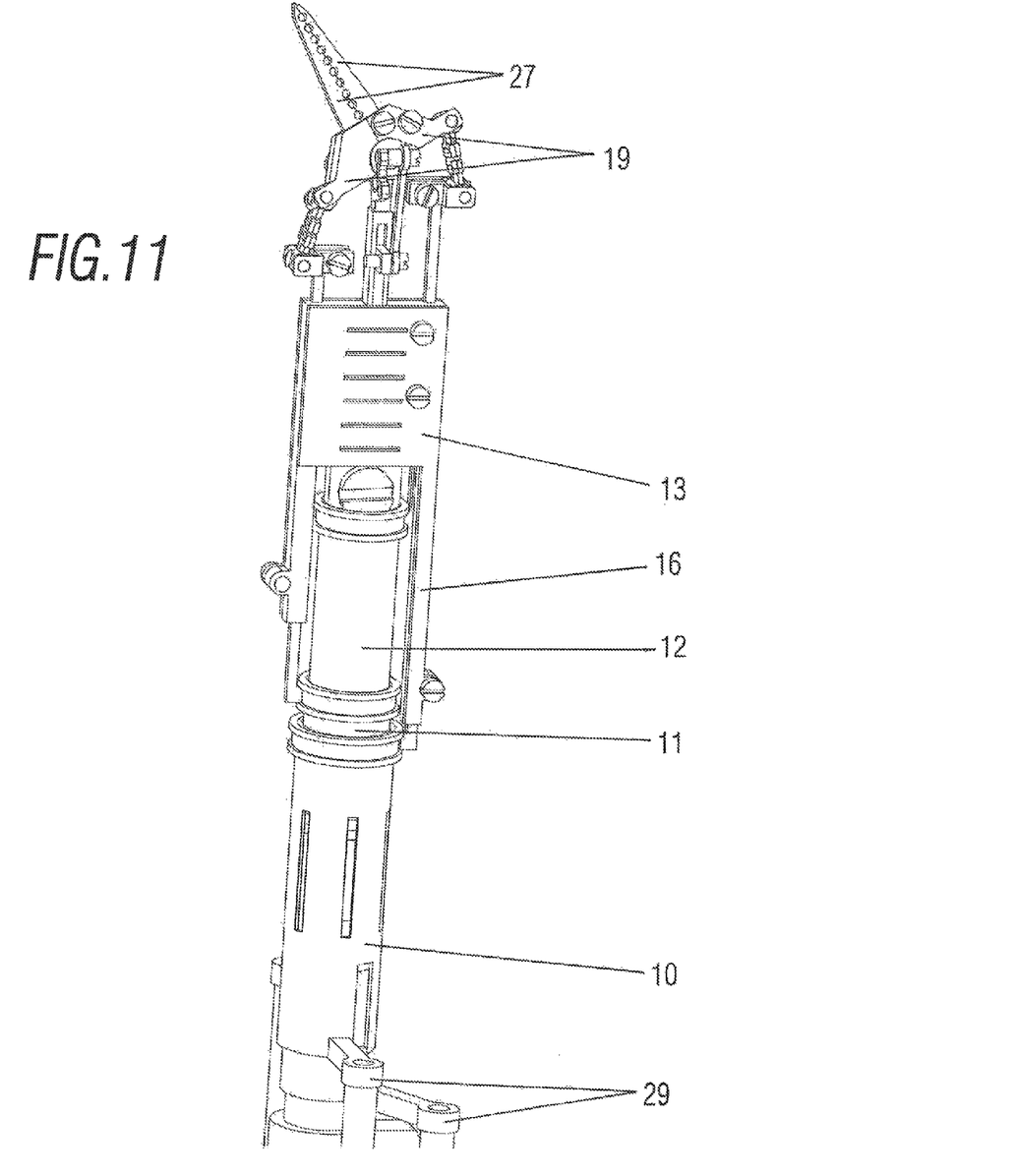
FIG. 11.—Perspective view of the section which houses the micro-tool, which is tilted.

In the embodiment shown here, the micro-tool 2 is comprised of a clamp provided with two gripping elements 27 facing each other, with each one of the gripping elements 27 associated with a respective articulation 18 of the third actuator. Advantageously, each of the gripping elements 27 is connected to a respective secondary servomotor 39, 42 (see FIGS. 5, 9A and 9B) to move independently from each other in relation to each gripping element 27, whose secondary servomotors 39 and 42 act independently from the first, second and third actuators. In this way, any of the gripping elements can remain in a position of maximal inclination such that only the other gripping element effects the clamp opening and closing operations, determining the distance between the gripping elements, for example, in a fully automated and previously defined manner and whose dimensional parameters can be viewed. In FIGS. 6A to 6F other formations or configurations are seen which the gripping elements can exhibit according to the needs or end use of the portable device of the invention.

Additionally, a series of miniaturised force sensors 37 may be provided, in particular four, in the bases of the respective piezoelectric servomotors, whereby the force and mechanical resistance offered by the object to be held or handled with the micro-tool can be accurately known. Thus, the control unit 7 may detect the possible loss of the clamped part (not shown), at the same time correcting the force and position in order to reset the object. The user can define the type of work being done and change the range of maximum force to be applied, and this is an especially important aspect when handling delicate objects or organisms, so that the force applied can be corrected at all times.

Another aspect to mention is the fact that the microprocessor 22 has the ability to automatically detect the existence of one or more nearby systems to work jointly or on a network, so that the device units may work on defined configurations jointly performing synchronised routines in order to perform synchronised actions. This function may prove particularly important in order to be able to work with a unit in each hand, for example, in surgical applications where a surgeon can perform coordinated synchronised work.

The aforementioned servomotors of the actuators are coupled to a structure 28, formed by interlaced tubular elements, which protrude from the main casing 3. As can be seen, the tubular elements of the structure 28 are fixed to the respective tubular bodies by means of a number of diametrically-protruding extensions 29. In particular, this structure 28 has a series of tubular elements, each one of them being integrally associated with each tubular body 10, 11 and 12, respectively.

In addition, the main casing 3 includes a display 30 that quickly and simply displays the data associated with the parameters regulated by the control unit 7, such as the level of horizontality, verticality or degree of incline, and a touch-type joystick 20 located at the front of the main casing 3 to control and navigate the positioning display menu.

The device has the capacity to memorise a specific spatial position and point, whose parameters are stored in the memory provided in the microprocessor and are obtained from the aforementioned gyroscopic sensor, motion detector and geomagnetic sensor. The data generated are of a point on the X, Y and Z space and horizontal, vertical and rotation incline positions in real time.

Since the microprocessor 22 has an internal algorithmic logic unit it may, at any time, by mathematical means and routinely in its internal program, know which variables are needed to go back and find a first memorised position as a reference point. The graphical representation of spatial position and its position in relation to the horizontal, vertical and rotational axes of the device is conducted on the existing display, by means of a programmed routine for the microprocessor, and wherein the latter is informed via digital data and analogical values of the sensors in real time, thereby generating a number of graphics that have been previously memorised in the control unit 7.

Although not described in the embodiment, it is evident that the control unit and servomotors include electronic components, electronic position encoders, etc. and circuitry which are suitable for correctly operating the actuation means, which are not represented to facilitate comprehension relative to the functioning of the stand-alone portable device.

As previously explained in reference to the force sensors, each of the first, second and third actuators comprise a resistance sensor device to control the force applied by the micro-tool, which consists of a thin sheet wherein a force or pressure value is converted into a resistance value. This value is adapted to a digital value via an internal converter, so that the mechanical force and resistance provided by the object to be held can be known with exact precision, wherein the microprocessor can control the minimum and maximum force to be applied as required in every action. By means of this, the microprocessor can detect the possible loss of the clamped part, at the same time correcting the force and position to reset the part to be handled. The user can define the type of work being done and change the range of minimum or maximum force to be applied, this aspect being important when handling delicate objects or organisms, and at all times the microprocessor can correct the force applied by means of closed loop by calculating the difference between the two halves of the micro-tool, such that the force can be corrected in real time by varying the pulses, depending on the measurement in a closing unit and monitoring the amount of force or resistance that is collected on the other side, in this case receiving, modifying its intensity and reversing the whole cycle if necessary.

Additionally, an electromagnetic device of reduced dimensions can be provided in order to polarise the tool (if it is a metallic material) with a positive or negative value sign which can be regulated by the user, thereby facilitating the fastening of very delicate elements.

Figure 12:
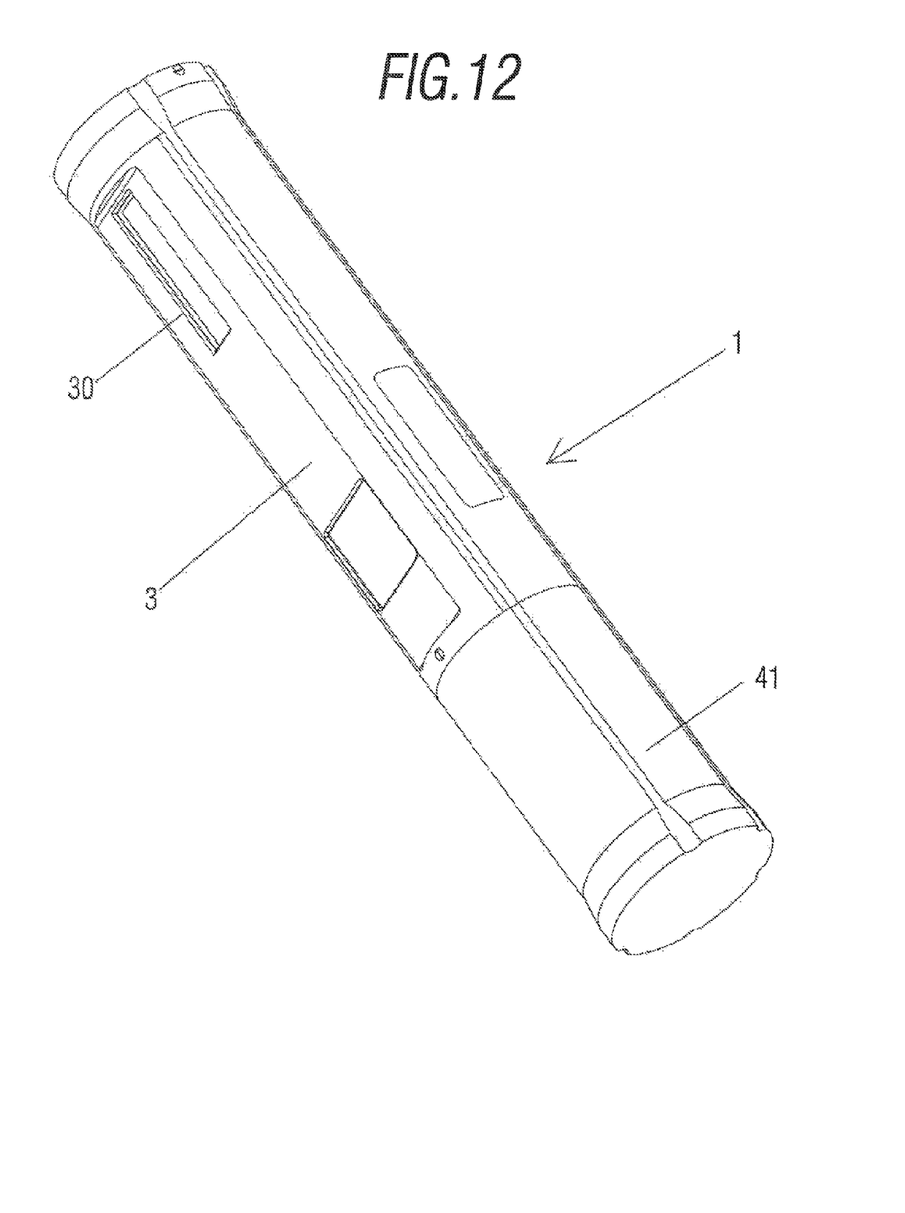
FIG. 12.—Perspective view of the portable device provided with a protective cap.

Finally, and in reference to FIG. 12, the portable device comprises a protective cap 41, preferably cylindrical in shape, which is engaged by snapping into place with the main casing 3 such that it covers the actuation means that protrude from outside the main casing 3 and the actual micro-tool 2.

The details, shapes and dimensions and other accessory elements as well as the materials used in the manufacture of the portable device of the invention may be conveniently replaced by others that are technically equivalent and do not depart from the essential nature of the invention or from the scope defined by the claims provided hereinafter.

The invention claimed is:

1. A portable standalone device, particularly suitable for use in surgery, micro-component handling and the like comprising a micro-tool that can be removably coupled to a main casing, and actuation means, fed autonomously by at least one battery, for handling the micro-tool, associated with servomotors, the micro-tool being comprised of a clamp provided with two gripping elements facing each other, the aforementioned actuation means comprising a first actuator associated with a first servomotor, providing the micro-tool with a degree of rotational freedom in respect of an axis which protrudes from the servomotor;

wherein the actuation means includes a second actuator associated with at least a second servomotor, connected to the first actuator which is suitable for moving the micro-tool forwards and backwards in translation; and a third actuator associated with a third servomotor, which is suitable for oscillating the micro-tool in relation to the longitudinal axis of the first and second actuators;

wherein the first, second and third actuators being associated with a control unit, housed in the main casing which can determine the position of the micro-tool in space;

in which each of the gripping elements of the micro-tool is associated with an articulation of the third actuator, each of the gripping elements being connected to a respective secondary actuator to perform mutually independent movements with respect to each gripping element, whose secondary servo-motors act independently from the first, second and third actuators;

wherein the second actuator comprises tubular bodies which can be extended telescopically between each other, inside of which the axis of the first actuator runs along, wherein each tubular body is connected to a separate servomotor and in which guide means are provided for rotationally moving the micro-tool, consisting said guiding means of grooves provided in each of the tubular bodies in which sections of a guide are inserted and arranged on the connector element that is displaceable along the entire diameter of the tubular bodies; and wherein the actuator servomotors are coupled in a structure that protrudes from the main casing, such that when a tubular body moves, the aforementioned structure moves, wherein tubular elements of the structures are fixed to respective tubular bodies by use of a number of diametrically protruding extensions.

2. A portable standalone device according to claim 1, wherein the micro-tool is attached to a connector element which is fixed to the axis of the first actuator.

3. A portable standalone device according to claim wherein the guide sections consist of L-shaped guide elements the end of which fit into both grooves.

4. A portable standalone device according to claim 1, wherein the third actuator comprises a pair of articulations which are attached to the connector element at one end and connected to the micro-tool at the opposite end.

5. A portable standalone device according to claim 4, wherein the pair of articulations is connected to the micro-tool via a tool holder which has fastening means for attaching the micro-tool.

6. A portable standalone device according to claim 1, wherein the control unit includes a support plate which is fixed inside the main casing.

7. A portable standalone device according to claim 1, wherein the control unit has a microprocessor having an associated programmable and electronic memory.

8. A portable standalone device according to claim 1, wherein the control unit includes a motion detector associated with the microprocessor for detecting the position and acceleration on three coordinate axes.

9. A portable standalone device according to claim 8, wherein the control unit includes automatic speech recognition to enter commands to the microprocessor.

10. A portable standalone device according to claim 8, wherein the microprocessor includes an arithmetic logic unit which can determine, in real time, the corrective positioning values to be applied in respect of the spatial position of the micro-tool at a given time.

11. A portable standalone device according to claim 1, wherein the control unit includes a gyroscopic sensor associated with the microprocessor to stabilise the position of the micro-tool on three coordinate axes.

12. A portable standalone device according to claim 11, wherein the parameters of spatial positioning of the micro-tool obtained from a gyroscopic sensor, motion detector and geomagnetic sensor can be viewed graphically by use of a display.

13. A portable standalone device according to claim 1, wherein the control unit includes a geomagnetic sensor on three coordinate axes X, Y and Z associated with the microprocessor to detect the spatial position in real time.

14. A portable standalone device according to claim 1, wherein the actuation means comprise at least a pushbutton located on an outer face of the main casing.

15. A portable standalone device according to claim 1, wherein the main casing includes a display which displays data associated with the parameters controlled by the control unit, including spatial positioning coordinate data and inclination of the micro-tool in real time.

16. A portable standalone device according to claim 1, wherein the control unit comprises a positioning navigation system and display menu provided with a touch-type joystick located in the main casing.

17. A portable standalone device according to claim 1, wherein an electro-magnetic device is provided for polarising the micro-tool with a positive or negative sign value which can be regulated.

18. A portable standalone device according to claim 1, wherein each of the first, second and third actuators comprise a resistance sensor device in order to control the force applied by the micro-tool on a part or object to be handled, said resistance sensor device being suitable for working between a maximum and minimum strength value range.

19. A portable standalone device according to claim 1, wherein said control unit is provided with wireless means for transmitting/receiving signals from at least one external device which works on a communications network.

20. A portable standalone device, particularly suitable for use in surgery, micro-component handling and the like comprising a micro-tool that can be removably coupled to a main casing, and actuation means, fed autonomously by at least one battery, for handling the micro-tool, associated with servomotors, the micro-tool being comprised of a clamp provided with two gripping elements facing each other, the aforementioned actuation means comprising a first actuator associated with a first servomotor, providing the micro-tool with a degree of rotational freedom in respect of an axis which protrudes from the servomotor;

wherein the actuation means include a second actuator associated with at least a second servomotor (36), connected to the first actuator which is suitable for moving the micro-tool forwards and backwards in translation; and a third actuator associated with a third servomotor, which is suitable for oscillating the micro-tool in relation to the longitudinal axis of the first and second actuators;

wherein the first, second and third actuators being associated with a control unit, housed in the main casing which can determine the position of the micro-tool in space; in which each of the gripping elements of the micro-tool is associated with an articulation of the third actuator, each of the gripping elements being connected to a respective secondary actuator to perform mutually independent movements with respect to each gripping element, whose secondary servo-motors act independently from the first, second and third actuators; and actuator servomotors are coupled in a structure that protrudes from the main casing, such that when the tubular body moves, the aforementioned structure moves, wherein the tubular elements of the structure are fixed to the respective tubular bodies by means of a number of diametrically protruding extensions.

\* \* \* \* \*